(12) United States Patent
Bombe et al.

(10) Patent No.: US 6,332,369 B1
(45) Date of Patent: Dec. 25, 2001

(54) DEVICE FOR COLLECTING GAS IN SEALED CONTAINERS THAT ARE TO BE CONTROLLED

(75) Inventors: Didier Bombe, Dury; Olivier Delebecque, La Chaussee Tirancourt, both of (FR)

(73) Assignee: AES Laboratoire, Societe Anonyme Ayant Son Siege Social, Combourg (FR)

(*) Notice: Subject to any disclaimer, the term of this patent is extended or adjusted under 35 U.S.C. 154(b) by 0 days.

(21) Appl. No.: 09/011,432

(22) Filed: Feb. 10, 1998

Related U.S. Application Data

(63) Continuation of application No. PCT/FR97/00958, filed on Jun. 2, 1997.

(30) Foreign Application Priority Data

Jun. 13, 1996 (FR) .................................................. 96 07355

(51) Int. Cl.$^7$ ................................................ G01N 1/00
(52) U.S. Cl. ........................................................ 73/864.73
(58) Field of Search .................................. 73/52, 863.85, 73/863.86, 864.41, 864.43, 864.74, 864.81, 863.21, 863.23

(56) References Cited

U.S. PATENT DOCUMENTS

| | | | |
|---|---|---|---|
| 3,186,232 | 6/1965 | Yates et al. | 73/421.5 |
| 3,206,982 | * 9/1965 | Blondfield | 73/863.85 |
| 3,374,678 | * 3/1968 | McGuckin | 73/863.85 |
| 3,412,613 | * 11/1968 | Brown et al. | 73/863.85 |
| 3,849,070 | 11/1974 | Garza et al. | 23/230 |
| 3,960,670 | 6/1976 | Pflug | 195/103.5 |
| 4,096,734 | 6/1978 | Khayat | 73/23.1 |
| 4,133,736 | 1/1979 | Nakagawa et al. | 204/195 |
| 5,131,283 | * 7/1992 | Canfield | 73/864.74 |
| 5,199,297 | * 4/1993 | Lin et al. | 73/52 |

FOREIGN PATENT DOCUMENTS

| | | | |
|---|---|---|---|
| 3439778 A1 | 4/1986 | (DE) | G01N/1/24 |
| 0 567 782 A1 | 11/1993 | (EP) | G01N/1/00 |
| 2 109 274 | 5/1972 | (FR) | G01N/21/00 |
| 2 711 803 A1 | 10/1993 | (FR) | G01N/33/0002 |
| 2 711 803 | 5/1995 | (FR) | G01N/33/02 |

* cited by examiner

Primary Examiner—Robert Raevis
(74) Attorney, Agent, or Firm—Michael R. Schacht; Hughes & Schacht, P.S.

(57) ABSTRACT

The device is characterized in that it comprises: one ring-shaped sensor (1) body comprising a main part (3) delimiting a sensor chamber (5) extended by a threaded part (6) as well as a skirt (4) around the sensing chamber (5) and defining a support surface (8) to be fixed on the wall (10) of the can or bag to be checked, a tubular connecting screw (2) coupled with continuous analyzing means and designed to cooperate with the sensor (1) body, and sensing means capable of cutting or perforating the wall (10) of the can or bag to be checked so as to allow the gases, if any emitted in this can or bag, to enter the internal conduit (11) of the connecting screw (2) to be sensed by the continuous analyzing means.

20 Claims, 3 Drawing Sheets

DEVICE FOR COLLECTING GAS IN SEALED CONTAINERS THAT ARE TO BE CONTROLLED

RELATED APPLICATIONS

This application is a continuation of PCT/FR97/00958 filed Jun. 2, 1997, which claims priority of French Application Ser. No. 96/07355 filed Jun. 13, 1996.

The present invention relates to a device for collecting gas in sealed containers that are to be controlled, and in particular in cans, especially small preserve cans, or in hermetically sealed flexible packs, such as, for example, packs of the TETRAPAK® type containing foodstuffs.

In order to guarantee consumer safety, the Authorities require that preserves be subjected to very strict controls, in particular defined by the AFNOR standards NFV 08 401 and NFV 08 402.

Those controls, which aim to check the consumable nature of preserves, basically involve placing several cans or jars from the same batch in an oven at a temperature favouring the development of micro-organisms, and then analysing their contents, after opening them, at the end of a specific incubation period.

Those analyses, which are especially measurements of differences in pH, are carried out in such case on a series of at least three cans, namely a control can, a can which has been incubated for seven days at 55° C. and a can which has been incubated for seven days at 37° C. or for twenty-one days at 32° C.

When the measured difference in pH is less than 0.5 and if no change in appearance or texture is detected, the preserve is considered to be stable and perfectly consumable; if this is not the case, the preserve is declared to be unfit for consumption and the entire batch has to be thrown away.

Under those conditions, and except where a deformation (swelling) of the analysed preserve cans is observed after emission of carbon dioxide due to microbe proliferation, the deterioration in the preserve cans is not detected until the end of the eighth or twenty-second day. This leads to obvious problems of loss and stock management.

In order to overcome that disadvantage, the document FR-A-93 12 829 has already proposed a device permitting continuous control of the contents of preserve cans in order to check the consumable nature thereof by collecting gases in the container or in the can without having to open it.

A disadvantage of the prior art device is associated with the fact that it cannot be adapted to all packaging and, in particular, to small preserve cans or flexible packs of the TETRAPAK® type, the use of which is becoming ever more widespread in the food industry.

The aim of the present invention is to overcome that disadvantage by proposing a device for collecting gas in sealed containers that are to be controlled, which device has the advantage of being both simple and universally applicable.

According to the invention, the device is characterised in that it comprises:
- an annular collector body composed of a substantially cylindrical principal portion delimiting, at its internal portion, a collecting chamber which is open to the outside and which is extended by a threaded portion, and of a collar surrounding the collecting chamber at its opposite end to the threaded portion and defining a support surface which is to be secured hermetically, especially adhesively bonded, to a wall of the can or pack to be controlled,
- a tubular connecting screw which is connected to continuous analysis devices and which is provided, on its external periphery, with a thread which is to cooperate with the threaded portion of the collector body in such a manner as to enable it to project into the collecting chamber by one of its ends or its first end, and
- collecting means which are capable of cutting or piercing the wall of the can or pack to be controlled at right-angles to the collecting chamber in order to enable any gases, especially carbon dioxide, emitted in the can or pack to penetrate via the opening so obtained into the chamber and then into the internal passage of the connecting screw so that they can be collected by the continuous analysis devices.

The device according to the invention is especially adapted to the control of packaging containing foodstuffs but could of course be used to control and analyse the contents of any sealed container, such as, for example, the contents of drums containing chemical products (solvents, paints, . . . ).

An important feature of the invention is associated with the fact that all the containers of a batch can be controlled simultaneously simply by securing the device to one of the containers of the batch.

By way of example, the continuous analysis devices may be constituted by devices capable of measuring and, where appropriate, representing graphically the variations as a function of time of the conductivity of a solution, especially a potash solution in contact with the collected gases, especially carbon dioxide.

This is a control by impedometry based on the fact that the conductivity of the solution analysed is a function of its concentration of $CO_2$, the principle of a control of this type is known per se.

According to a further feature of the invention, the collecting means comprise, on the one hand, perforating devices closing the internal passage of the connecting screw in the area of the first and thereof and, on the other hand, receiving ducts connecting the passage to the collecting chamber.

The nature of the perforating devices of course depends on the type of material that is to be pierced or cut; by way of example, it is possible to use a single tip but also a set of two tips effecting the cutting of a circular orifice, following the rotation of the connecting screw, or a tip having a configuration of the drill bit type.

According to the invention, the receiving ducts are generally distributed over the periphery of the connecting screw, in the immediate vicinity of the first end thereof; by way of variation, they may also be placed in the area of the first end of the connecting screw, between several tips.

It should also be noted that, depending on the nature of the container to be controlled, the device may be for one-off use and may be mounted routinely on the container, in which case the collector body is generally produced from plastics material. The device may also be intended for repeated use, the collector body then generally being produced from metal; in the latter case, the user must himself adhesively bond the support surface of the collector body to the wall of the container after previously disinfecting the latter in order to prevent any contamination which could distort the results obtained.

During the mounting of the device, whether this is effected in the factory or by the user at the time the control is to be carried out, the connecting screw is generally introduced into the annular collector body in a position in which the receiving ducts open at right-angles into the threaded portion of the body.

From that rest position, and according to a basic feature of the invention, the connecting screw can be displaced, by rotation at the internal portion of the collector body, between, on the one hand, a collecting position in which the perforating devices are capable of cooperating with the wall of the container or pack to be controlled in order to pierce or cut the wall and, on the other hand, a control position in which the opening so obtained is freed and the receiving ducts open into the collecting chamber so that any gases, and especially carbon dioxide, emitted in the container or pack to be controlled can penetrate into the chamber and then into the internal passage of the connecting screw so that they can be collected by the continuous analysis devices.

Tests carried out in a production unit have shown that the average time taken to detect contamination is 48 hours. For security, it is expedient to prolong the test for approximately four days, which nevertheless constitutes a substantial time-saving compared with the devices according to the prior art.

The device according to the invention therefore enables the deterioration in cans or packs belonging to the same batch to be detected very rapidly, so that it is possible to treat the causes of deterioration as soon as possible in the production chain and to limit the number of cans or packs that are unfit for consumption and that have to be destroyed.

The value of the device will therefore be readily appreciated.

According to a further basic feature of the invention, the internal passage of the connecting screw is closed, especially in the area of the second end opposite the first end, by a principal seal equipped with a filtering membrane which is permeable to gases but impermeable to micro-organisms and especially to pathogenic germs.

The filtering membrane is in fact an indispensable element of the devices according to the invention given that it ensures the impermeability of the collecting chamber with respect to micro-organisms coming from the external medium during the analysis process so as to exclude any risk of contaminating the internal portion of the container or pack, which could distort the results obtained.

it should be noted that the principal seal may, by way of example, be designed in the form of a plug provided with an end-part for adapting the continuous analysis devices.

According to a further feature of the invention, the connecting screw is provided, in the area of its second end, with a thickened portion which comprises, on its external face, a peripheral groove receiving an O-ring seal supported against the internal face of a sealing chamber which is open to the outside and which is arranged in the extension of the threaded portion of the collector body, in order to ensure the impermeability of the collecting chamber with respect to the external medium.

The features of the device for collecting gas in sealed containers, which forms the subject-matter of the invention, are described in more detail with reference to the appended drawings in which:

DETAILED DESCRIPTION OF THE DRAWING

The following description is given with consideration of the particular case in which the device is to be used for the continuous control of the stability of a preserve can in order to check the consumable nature thereof. As has already been indicated, this example is in no way to be regarded as limiting the invention, and the collecting device forming the subject-matter of the invention could be used to control the contents of other types of container.

Figure 1:
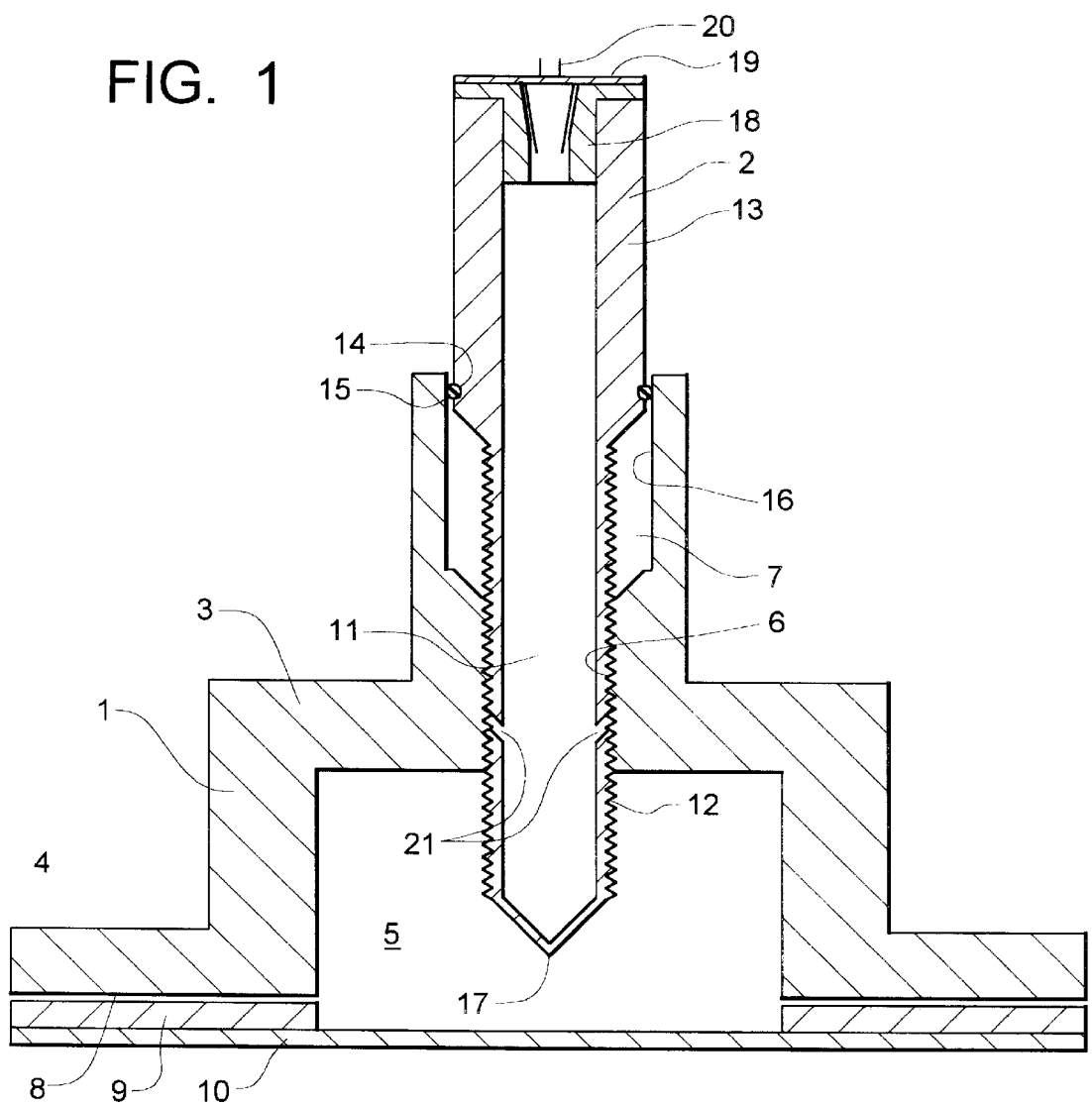
FIG. 1 is a diagrammatic section representing the device in the rest position.

According to FIG. 1, the device substantially comprises an annular collector body 1 and a tubular connecting screw 2.

The collector body 1 comprises a substantially cylindrical principal portion 3 which is extended at its lower portion by a collar 4.

It should be noted that in the course of this explanation the adjectives "upper" and "lower" refer to the preserve can in the normal upright storage position.

The principal portion 3 of the collector body 1 delimits, at its internal portion, a collecting chamber 5 which is open to the outside at its lower portion and which is extended at its upper portion by a threaded portion 6 and then by a sealing chamber 7 which is open to the outside at its upper portion.

The collar 4 surrounds the collecting chamber 5 and comprises, at its lower portion, a support surface 8 by which the device is secured hermetically to a wall 10 of the preserve can to be controlled by means of a layer of adhesive 9.

According to FIG. 1, the connecting screw 2 is provided, on its external periphery, on the one hand at its lower portion, with a thread 12 cooperating with the threaded portion 6 of the collector body 1 and, on the other hand at its upper portion, with a thickened portion 13 comprising an external peripheral groove 14 which receives an O-ring seal 15 supported against the internal face 16 of the sealing chamber 7.

The internal passage 11 of the connecting screw 2 is for its part closed at its lower end by perforating devices 17 in the form of a tip projecting into the collecting chamber 5 and, at its upper portion, by a principal seal 18 which forms a plug and which is equipped with a filtering membrane 19 permeable to gases but impermeable to micro-organisms and especially to pathogenic germs.

An adapting end-part 20 provided on the seal 18 enables continuous analysis devices, not represented in the Figures, to be mounted thereon.

According to FIG. 1, receiving through-ducts 21 are distributed over the periphery of the connecting screw 2 in the immediate vicinity of the perforating devices 17.

In the rest position, represented in FIG. 1, the receiving ducts 21 open at right-angles into the threaded portion 6 of the collector body 1.

Figure 2:
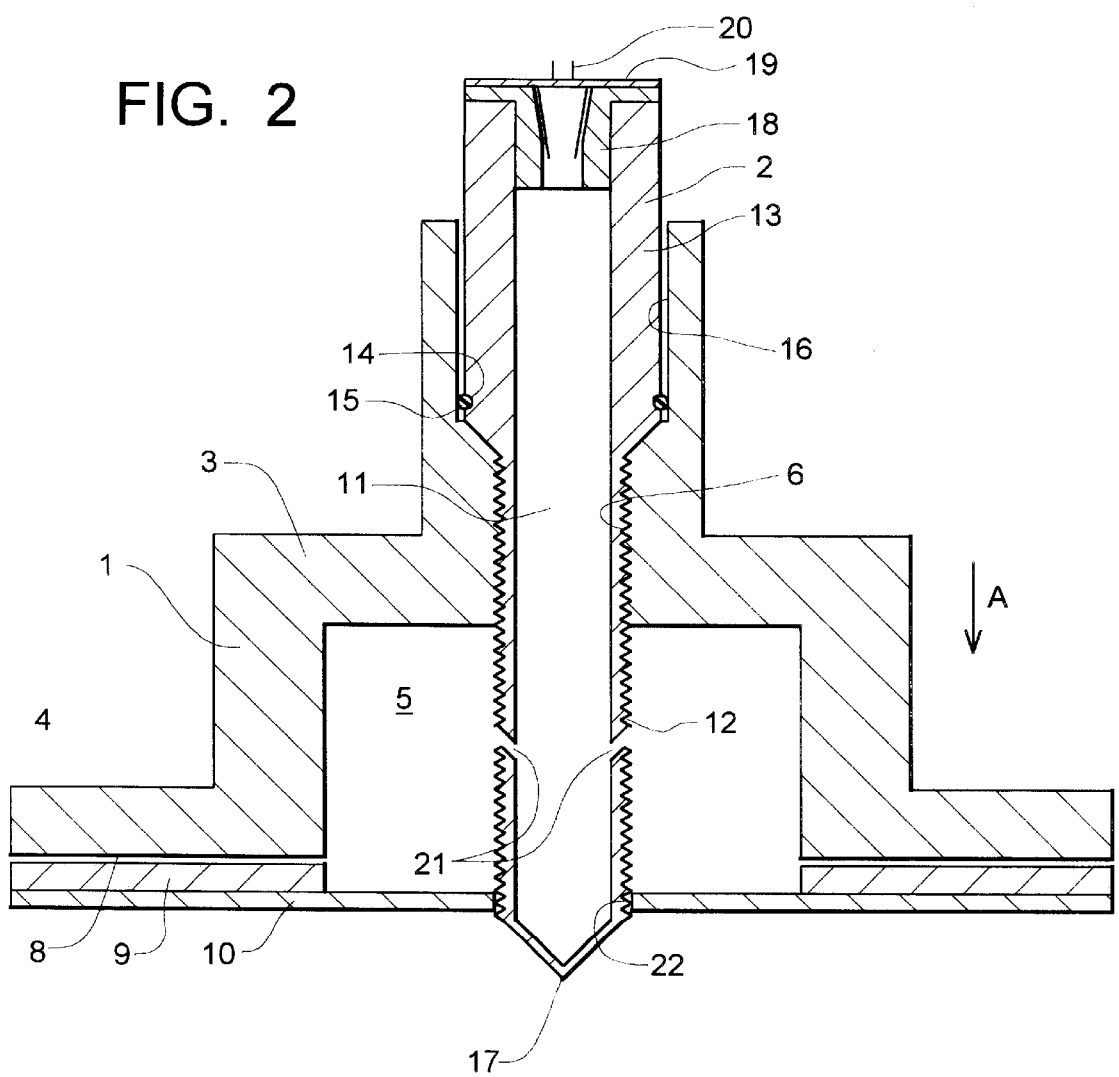
FIG. 2 is a section corresponding to FIG. 1 but representing the device in the collecting position.

Starting from the rest position and as shown in FIG. 2, the user can displace the connecting screw 2 downwards in the direction of arrow A by turning it in the threaded portion 6 of the collector body 1 until it reaches a position in which the perforating devices 17 come into contact with the wall 10 of the preserve can to be controlled, and can then continue this displacement until an opening 22 has been pierced in the wall 10.

Figure 3:
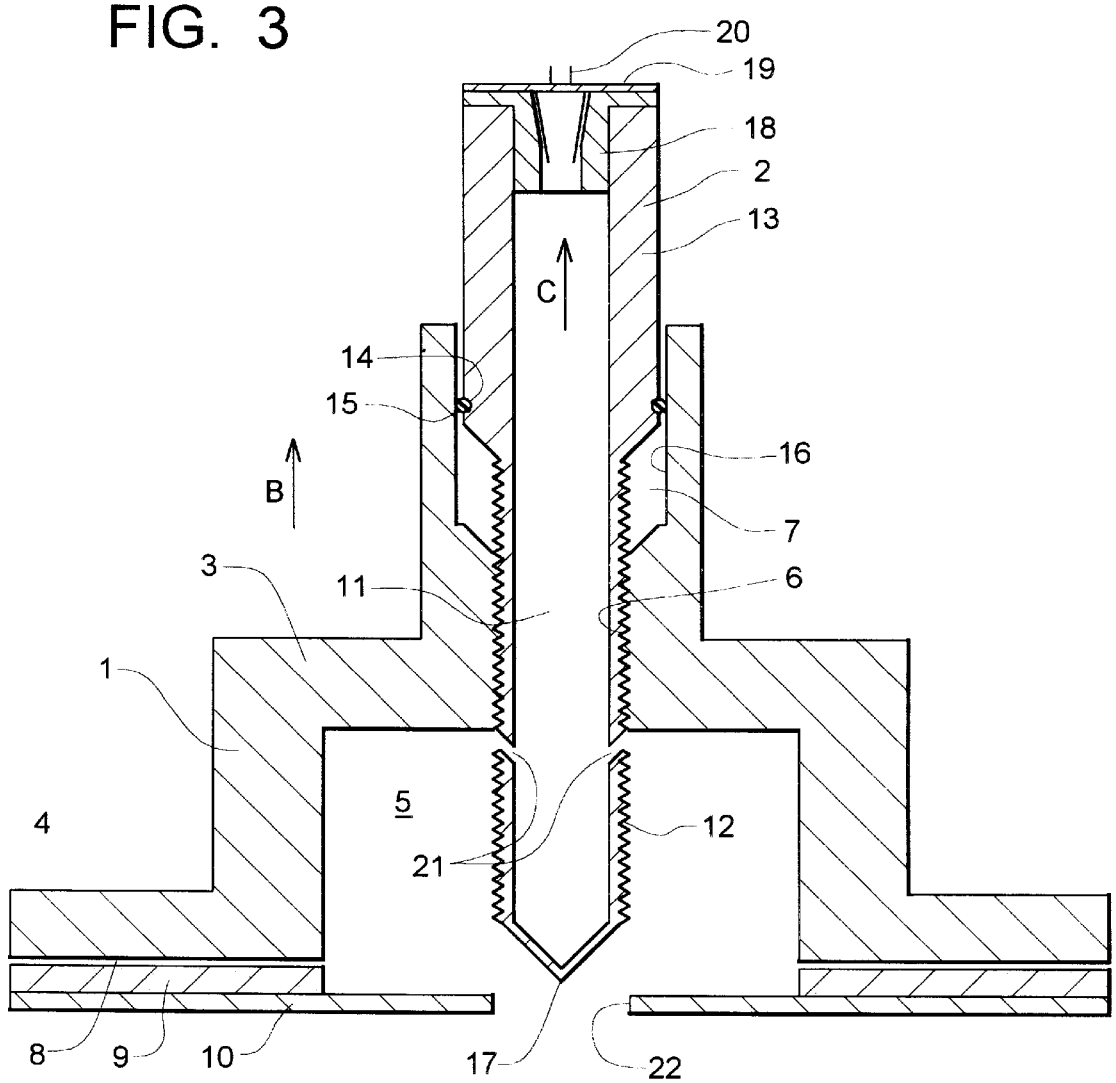
FIG. 3 is a section corresponding to FIGS. 1 and 2 but representing the same device in the control position.

From that position, the user can then raise the connecting screw 2 in the direction of arrow B, in the opposite direction to arrow A, into a control position represented in FIG. 3; in that position, the opening 22 is freed and the receiving ducts 21 open into the collecting chamber 5.

According to FIG. 3, any gases emitted inside the preserve can 10 can therefore escape and penetrate into the collecting chamber 5 via the previously pierced opening 22, and then into the internal passage 11 of the connecting screw 2, passing via the receiving ducts 21, to arrive, as indicated by arrow C, at the continuous analysis devices through the principal seal 18; the presence of the seal 18 prevents the results of the control from being distorted after the penetration, into the can 10, of micro-organisms coming from the external medium. The O-ring seal 15 also contributes to an excellent impermeability of the collecting chamber 5 with respect to the outside.

What is claimed is:

1. A system for collecting gas emitted for foodstuffs contained within a sealed container for continuous analysis by an analysis device, the system comprising:
    a collector body defining a collecting chamber arranged between first and second openings in the collector body, where the collector body further defines a threaded portion within the collecting chamber and a collar extending around the second opening in the collector body, the collar being secured to a wall of the sealed container;
    a connecting screw defining an internal passage, a perforating portion, a threaded portion, and at least one receiving duct for allowing fluid communication with the internal passage, where
        the connecting screw extends into the collecting chamber through the first opening such that the perforating portion is arranged within the collecting chamber, and
        the threaded portion of the connecting screw cooperates with the threaded portion of the collector body such that rotation of the connecting screw moves the connecting screw relative to the collecting body; and
    a main seal assembly mounted on the connecting screw and operatively connected to the analysis device, the main seal assembly comprising a filtering membrane that is permeable to gasses and impermeable to micro-organisms, where the filtering membrane is arranged such that fluid flowing through the internal passage passes through the filtering membrane; whereby
        rotation of the connecting screw in a first direction causes the connecting screw to move towards the wall of the sealed container such that the perforating portion of the connecting screw engages the wall of the sealed container and forms a container opening that is surrounded by the collar of the collector body; and
        rotation of the connecting screw in a second direction causes the connecting screw to move away from the wall of the sealed container such that gases within the sealed container flow through the container opening, into the collecting chamber, through the receiving duct, internal passage, and filtering membrane, and to the analysis device.

2. A system as recited in claim 1, in which a plurality of receiving ducts are formed in the connecting screw.

3. A system as recited in claim 1, in which the at least one receiving duct is arranged adjacent to the perforating portion of the connecting screw.

4. A system as recited in claim 2, in which the plurality of receiving ducts are arranged adjacent to the perforating portion of the connecting screw.

5. A system as recited in claim 1, further comprising a screw seal arranged to form a seal between the connecting screw and the collector body.

6. A system as recited in claim 1, in which the connecting screw further comprises a thickened portion, where the threaded portion of the connecting screw is arranged between the perforating portion of the connecting screw and the thickened portion of the connecting screw.

7. A system as recited in claim 5, in which the connecting screw further comprises a thickened portion, where the threaded portion of the connecting screw is arranged between the perforating portion of the connecting screw and the thickened portion of the connecting screw and the screw seal engages the thickened portion of the connecting screw.

8. A system as recited in claim 5, in which a groove is formed in the connecting screw to retain the screw seal in a desired orientation relative to the connecting screw.

9. A system as recited in claim 7, in which a groove is formed in the thickened portion of the connecting screw to retain the screw seal in a desired orientation relative to the connecting screw.

10. A system as recited in claim 1, in which:
    the collecting chamber is partially defined by a sealing surface formed on the collector body, where the sealing surface on the collector body is arranged between the first opening in the collector body and the threaded portion on the collector body;
    the connecting screw further comprises a thickened portion, where the thickened portion of the connecting screw is arranged between the main seal assembly and the threaded portion of the connecting screw; and
    a screw seal member is arranged to engage the thickened portion of the connecting screw and the sealing surface on the collector body to prevent fluid flow between the connecting screw and the collector body.

11. A system as recited in claim 10, in which a groove is formed in the thickened portion of the connecting screw to retain the screw seal in a desired orientation relative to the connecting screw.

12. A system as recited in claim 10, wherein the thickened portion of the collecting screw at least partially resides in a portion of the collecting chamber defined by the sealing surface on the collector body.

13. A system as recited in claim 1, further comprising adhesive for bonding the collar to the wall of the sealed container.

14. In a system comprising:
    a collector body defining a collecting chamber arranged between first and second openings in the collector body, where the collector body further defines a threaded portion within the collecting chamber and a collar extending around the second opening in the collector body;
    a connecting screw defining an internal passage, a perforating portion, a threaded portion, and at least one receiving duct for allowing fluid communication with the internal passage, where
        the connecting screw extends into the collecting chamber through the first opening such that the perforating portion is arranged within the collecting chamber, and
        the threaded portion of the connecting screw cooperates with the threaded portion of the collector body such that rotation of the connecting screw moves the connecting screw relative to the collecting body; and
    a main seal assembly mounted on the connecting screw, the main seal assembly comprising a filtering membrane that is permeable to gasses and impermeable to micro-organisms, where the filtering membrane is arranged such that fluid flowing through the internal passage passes through the filtering membrane;

a method of continuously analyzing gas emitted from foodstuffs contained within a sealed container comprising the steps of:

adhering the collar to a wall of the sealed container to close the second opening in the collector body;

rotating the connecting screw in a first direction to cause the connecting screw to move towards the wall of the sealed container such that the perforating portion of the connecting screw engages the wall of the sealed container to form a container opening in the wall of the sealed container; and rotating the connecting screw in a second direction to cause the connecting screw to move away from the wall of the sealed container; and operatively connecting the main seal assembly to the analysis device such that gases within the sealed container flow through the container opening, into the collecting chamber, through the receiving duct, internal passage, and filtering membrane, and to the analysis device for analysis.

15. A method as recited in claim 14, further comprising the step of arranging a screw seal between the connecting screw and the collector body.

16. A system for collecting gas emitted from foodstuffs contained within a sealed container for continuous analysis by an analysis device, the system comprising:

a collector body defining a collecting chamber arranged between first and second openings in the collector body, where the collector body further defines a threaded portion within the collecting chamber and a collar extending around the second opening in the collector body;

a connecting screw defining an internal passage, a perforating portion, a threaded portion, and at least one receiving duct for allowing fluid communication with the internal passage, where the connecting screw extends into the collecting chamber through the first opening such that the perforating portion is arranged within the collecting chamber, and the threaded portion of the connecting screw cooperates with the threaded portion of the collector body such that rotation of the connecting screw moves the connecting screw relative to the collecting body; and a main seal assembly mounted on the connecting screw and operatively connected to the analysis device, the main seal assembly comprising a filtering membrane that is permeable to gasses and impermeable to microorganisms, where the filtering membrane is arranged such that fluid flowing through the internal passage passes through the filtering membrane;

a screw seal member arranged between the collector body and the connecting screw to prevent fluid flow between the collector body and the connecting member; and adhesive for securing the collar to a wall of the sealed container; whereby rotation of the connecting screw in a first direction causes the connecting screw to move towards the wall of the sealed container such that the perforating portion of the connecting screw engages the wall of the sealed container and forms a container opening that is surrounded by the collar of the collector body; and rotation of the connecting screw in a second direction causes the connecting screw to move away from the wall of the sealed container such that gases within the sealed container flow through the container opening, into the collecting chamber, through the receiving duct, internal passage, and filtering membrane, and to the analysis device.

17. A system as recited in claim 16, in which a plurality of receiving ducts are formed in the connecting screw adjacent to the perforating portion of the connecting screw.

18. A system as recited in claim 16, in which the connecting screw further comprises a thickened portion, where the threaded portion of the connecting screw is arranged between the perforating portion of the connecting screw and the thickened portion of the connecting screw and the screw seal engages the thickened portion of the connecting screw.

19. A system as recited in claim 18, in which a groove is formed in the thickened portion of the connecting screw to retain the screw seal in a desired orientation relative to the connecting screw.

20. A system as recited in claim 16, in which:

the collecting chamber is partially defined by a sealing surface formed on the collector body, where the sealing surface on the collector body is arranged between the first opening in the collector body and the threaded portion on the collector body;

the connecting screw further comprises a thickened portion, where the thickened portion of the connecting screw is arranged between the main seal assembly and the threaded portion of the connecting screw; and the screw seal member is arranged to engage the thickened portion of the connecting screw and the sealing surface on the collector body to prevent fluid flow between the connecting screw and the collector body.

\* \* \* \* \*